US007888022B2

(12) United States Patent
Poupon et al.

(10) Patent No.: US 7,888,022 B2
(45) Date of Patent: *Feb. 15, 2011

(54) SCREENING OF A NOVEL HEPATIC SYNDROME AND ITS USES

(75) Inventors: Raoul Poupon, Paris (FR); Brigitte Hermelin, Versailles (FR); Olivier Rosmorduc, Paris (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/878,420

(22) Filed: Jul. 24, 2007

(65) Prior Publication Data

US 2008/0095858 A1 Apr. 24, 2008

Related U.S. Application Data

(60) Division of application No. 10/360,705, filed on Feb. 10, 2003, now Pat. No. 7,262,011, which is a continuation-in-part of application No. PCT/FR01/02553, filed on Aug. 6, 2001.

(30) Foreign Application Priority Data

Aug. 8, 2000 (FR) .................................. 00 10428

(51) Int. Cl.
C12Q 1/68 (2006.01)
C12P 19/34 (2006.01)
C07H 21/02 (2006.01)
C07H 21/04 (2006.01)

(52) U.S. Cl. .................. 435/6; 435/91.2; 536/23.5; 536/24.31; 536/24.33

(58) Field of Classification Search ........................ None
See application file for complete search history.

(56) References Cited

U.S. PATENT DOCUMENTS 7,262,011 B2 * 8/2007 Poupon et al. ................. 435/6

OTHER PUBLICATIONS

Halushka et al. Nature. Jul. 1999. 22: 239-247.*
Lang et al. Drug Metabolism and Disposition. 2006. 34:1582-1599.*
P.H. Dixon et al.: "Heterozygous MDR3 Missense Mutation Associated With Intrahepatic Cholestasis of Pregnancy: Evidence for a Defect in Protein Trafficking", Human Molecular Genetics, vol. 9(8), pp. 1209-1217, 2000.
J. Marleen L. De Vree et al.: "Mutations in the *MDR3* Gene Cause Progressive Familial Intrahepatic Cholestasis", Proc. Natl. Acad. Sci. USA, vol. 95, pp. 282-287, 1998.
Emmanuel Jacquemin et al.: "Heterozygous Non-Sense Mutation of the MDR3 Gene in Familial Intrahepatic Cholestasis of Pregnancy", The Lancet, vol. 353, pp. 210-211, 1999.
Emmanuel Jacquemin et al.: "Genetic Basis of Progressive Familial Intrahepatic Cholestasis", Journal of Hepatology, vol. 31(2), pp. 377-381, 1999.
E. Jacquemin et al.: "MDR3 Deficiency in Patients with Progressive Familial Intrahepatic Cholestasis with High Serum Gamma-Glutamyl Transferase (GGT) Activity (PFIC3)", Journal of Pediatric Gastroenterology and Nutrition, vol. 31, pp. 207 (abstract), 2000.
Jacquemin et al.: "The Wide Spectrum of Multidrug Resistance 3 Deficiency: From Neonatal Cholestasis to Cirrhosis of Adulthood", Gastroenterology, vol. 120, pp. 1448-1458, 2001.
Lincke et al.: "Structure of the Human *MDR3* Gene and Physical Mapping of the Human *MDR* Locus", The Journal of :Biological Chemistry, vol. 266(8), pp. 5303-5310, 1991.
Rosmorduc et al.: "MDR3 Gene Defect in Adults with Symptomatic Intrahepatic and Gallbladder Cholesterol Cholelithiasis", Gastroenterology, vol. 12, pp. 1459-1467, 2001.
Rosmorduc et al.: "MDR3 Gene Defect in Adults with a Peculiar Variant of Cholesteral", Journal of Hepatology, vol. 34 (supplement 1), p. 188, 2001.

* cited by examiner

*Primary Examiner*—Carla Myers
(74) *Attorney, Agent, or Firm*—Morgan, Lewis & Bockius LLP

(57) ABSTRACT

The invention concerns methods of screening for a hepatic syndrome occurring in the young adult and associating cholesterol biliary microlithiasis, intrahepatic cholestasis and several mutations of the MDR3 gene. The invention is also directed to methods for the treatment of said syndrome. The hepatic syndrome screening methods comprise detecting, from a nucleic acid sample extracted from peripheral blood mononucleate cells, heterozygous mutations of the MDR3 gene and/or homozygous mutations of the MDR3 gene that do not eliminate the expression of the protein expressed by the MDR3 gene, which has phosphatidylcholine carrier activity, in adult subjects associating cholesterol biliary microlithiasis and intrahepatic cholestasis.

4 Claims, 4 Drawing Sheets

SCREENING OF A NOVEL HEPATIC SYNDROME AND ITS USES

RELATED APPLICATIONS

This is a divisional of application Ser. No. 10/360,705, filed Feb. 10, 2003, now U.S. Pat. No. 7,262,011, which is a continuation-in-part of international application PCT/FR01/02553, filed Aug. 6, 2001 which claims priority to French application 00/10428, filed Aug. 8, 2000 All of the foregoing documents are hereby expressly incorporated by reference in their entireties into the present application.

The present invention relates to the screening of a hepatic syndrome occurring in young adults and associating (i) intrahepatic hyperechoic foci with or without intrahepatic sludge or microlithiasis and further on a cholesterol microcholelithiasis, intrahepatic cholestasis and (ii) one or more mutations of the MDR3 gene (point mutations and/or SNPs).

The present invention also relates to the treatment of said syndrome.

Cholesterol cholelithiasis is characterized by the presence of calculi of cholesterol or of calcium bilirubinate. Cholesterol lithiasis is the most common form of cholelithiasis (80%). It is characterized by the formation of calculi of cholesterol in the gall bladder, due to an excess of bile cholesterol compared to solubilizing molecules, namely bile acids and phospholipids. Its prevalence is estimated, taking all ages into account, to be 10 to 20% of the population in industrialized countries. It is more prevalent in women and increases considerably with age (40% in women over the age of 60). Gall bladder lithiasis can be a source of complications: cholecystitis, cancer of the gall bladder, migration of calculi in the common bile duct, a cause of angiocholitis and of pancreatitis. Treatment for this diseases is based mainly on surgery: cholecystectomy by laparotomy or celioscopy, biliary drainage with peroperative or perendoscopic extraction of the common bile duct calculi. Medical treatment, which consists of administering chenodeoxycholic acid and/or ursodeoxycholic acid, is reserved for forms of non-complicated cholesterol cholelithiasis of the gall bladder.

Chronic biliary cholestasis is characterized by a deficiency in passage of the bile from the liver to the extrahepatic bile ducts and the intestine. The causes and physiopathology are varied (Poupon et al., 2000, *J. Hepatol.*, 32, 129-140). Most chronic biliary cholestases can progress to biliary cirrhosis and hepatocellular insufficiency requiring a liver transplant.

In children for example, cholestasis is observed in biliary atresia, in Alagille syndrome or in progressive familial intrahepatic cholestasis (PFIC). In general, genetic abnormalities are observed in these various diseases.

Familial intrahepatic cholestasis (PFIC) are infantile recessive diseases which are characterized by intermittent jaundice, severe cholestasis and cirrhosis, with a fatal outcome during the first ten years of life.

These diseases manifest themselves in several clinical forms, two of which are determined by mutations present on genes encoding ABC transporters. Byler's disease, or progressive familial intrahepatic cholestasis type 1, which is characterized by normal cholesteremia and normal serum γ-glutamyl transferase activity, was the first described. It is caused by mutation of the FIC1 gene, a type V ATPase involved in phospholipid transport from the outer wall to the inner wall of various cell membranes. More specifically, PFIC type 1 is characterized by recurrent episodes of jaundice, severe pruritis, normal γ-GT activity and normal cholesterol levels, high concentrations of bile acids in the serum and low levels of bile acids in the bile. The PFIC1 locus was found in chromosome 18q21-q22; five mutations were identified: a deletion, a deleted exon and three missense mutations; these missense mutations concern domains which are highly conserved in type V ATPases (E. Jacquemin et al., J. Hepatol., 1999, 31, 377-381).

Familial cholestasis type 2 exhibits the same clinical signs of Byler's disease, but it is caused by mutations in the FIC2 gene, which encodes the BSEP (Bile Salt Export Pump) transporter. This gene is the homolog of the murine SPGP gene, the product of which, expressed exclusively in hepatocytes, is involved in bile salt transport. PFIC type 3 is characterized by a severe pruritis, normal γ-GT activity and a normal cholesterol level in the serum, high concentrations of bile acids in the serum and very low levels of bile acids in the bile. The PIFC2 locus was found in chromosome 2q24: 10 mutations were identified, including deletions and missense mutations involving important domains of the BSEP transporter (E. Jacquemin et al., J. Hepatol., 1999, 31, 377-381).

Individuals suffering from progressive familial intrahepatic cholestasis type 3 (PFIC3) have mutations in the MDR3 gene. PFIC type 3 differs from the other PFICs in particular by the fact that it has a high serum γ-glutamyl transferase activity. The MDR (Multi Drug Resistance) family of ABC transporters is a multigene family of homologous proteins, some of which (MDR3) are not involved in drug resistance, and are phosphatidylcholine transporters. The MDR3 gene, revealed in 1993, is a phospholipid translocator. It is expressed in hepatocytes and provides phosphatidylcholine translocation, thus leading to secretion of this phospholipid into the bile.

Mice in which the gene equivalent to MDR3 has been knocked out, mdr 2 (−/−), exhibit a deficiency secretion of phospholipids into the bile, which causes physiological modifications close to those patients suffering from progressive familial intrahepatic cholestasis type 3. Two patients suffering from this disease and carrying mutations on both MDR3 alleles have recently been described; the histopathological profile of the two patients is similar to that observed in the mdr 2 (−/−) mice (J. Marleen L. de Vree et al., PNAS, 1998, 95, 1, 282-287). More specifically, at the histological level, portal fibrosis, proliferation in the bile ducts and the presence of an inflammatory infiltrate are observed. However, no cholesterol microcholelithiasis is observed in these patients suffering from PFIC3 or in the mdr 2 (−/−) mice. At the gene level, in the first patient, a homozygous 7 bp deletion was observed, beginning at amino acid 132, leading to a reading frame shift and introducing a stop codon, 29 codons downstream; the second patient is homozygous for a nonsense mutation in codon 957 (C/T) which introduces a stop codon (TGA): this mutation deletes the TaqI restriction site. In such a pathological condition, truncated, nonactive proteins, missing at least one ABC motif, are expressed. Furthermore, additional nonsense mutations and missense mutations, associated with very low levels of bile phospholipids, have also been observed.

Cholestasis appearing only during pregnancy have also been observed in patients exhibiting a heterozygous mutation of the MDR3 gene; in such cases, no microlithiasis has been observed (E. Jacquemin et al., The Lancet, 1999, 353, 210-211; Dixon et al., Human Molecular Genetics, 2000, 9, 1209-1217).

More specifically, in these patients, the following are observed:

either a heterozygous deletion of a nucleotide (1712delT) beginning at amino acid 571, leading to a reading frame shift introducing a stop codon, 15 codons downstream: this mutation, which leads to the expression of a truncated, nonactive protein, was detected in pregnant women from a family suffering from PFIC3 (Jacquemin et al., The Lancet, 1999, mentioned above);

or a missense mutation in exon 14 (A546D): this mutation was detected in pregnant women with no family history of PFIC (Dixon et al., mentioned above).

Surprisingly, the inventors have found that, in young adults (20-40 years old), pathological conditions exist which differ from PFIC type 3, which are triggered under situations such as pregnancy, the taking of sex hormones, sustained fasting, sustained parenteral nutrition, and surgical interventions, or by hepatotoxic cofactors (obesity, diabetes, the taking of medicines liable to modify the composition of bile: fibrates or diuretics, in particular), and in which the following are observed in combination:

cholesterol microcholelithiasis
intrahepatic cholestasis and
at least one mutation of the MDR3 gene (point mutation and/or SNPs).

The onset of this syndrome is related to the appearance, before microlithiasis, of intrahepatic hyperechoic foci with or without intrahepatic sludge.

In this syndrome, a deficiency in bile phospholipids is observed (abnormality of bile phospholipid secretion), limiting the solubilization of cholesterol and leading to the precipitation thereof in the form of microcalculi in situ within the small bile ducts and, in extreme forms, within the entire biliary tree.

These microcalculi, which can be detected through examination of the liver by ultrasonography, exhibit the following characteristics:

they are observed in the form of multiple calculi which are small in size (<2 mm), present in the intrahepatic bile ducts,
they are sensitive to treatment with ursodeoxycholic acid (UDCA); this treatment makes it possible to obtain rapid disappearance of the symptoms, unlike cholecystectomy, which leads to a recurrence of the disease. This recurrence can, however, be prevented by administering UDCA, and
they differ from gall bladder calculi by their small size, their location and their sensitivity to treatment with UDCA.

The very large decrease in the concentration of bile phospholipids, and the presence of cholesterol crystals sensitive to treatment with UDCA, combined with a mutation of the MDR3 gene, characterize this syndrome. This syndrome is now referred to as Low Phospholipid Associated Cholelithiasis (LPAC).

The screening and the prevention of this pathological condition, which is different from PFIC type 3, in individuals having personal or family history of gall bladder lithiasis or of unexplained hepatic ailments (biological abnormalities relating to tests for cholestasis increase in serum activity of γ-glutamyltranspeptidases, transaminases) are crucial. Specifically, 10 to 20% of gravid cholestasis might, in fact, correspond to this syndrome, and its morbidity, including repeat abortions, might thus be avoided in the case of good screening and effective prevention.

For this reason, the inventors gave themselves the aim of providing a test for screening this pathological condition, which differs from progressive familial intrahepatic cholestasis type 3 (PFIC3) both clinically and biochemically, in such a way as to prevent its harmful effects, in particular in women of childbearing condition.

A subject-matter of the present invention is a method for the screening of a hepatic syndrome, characterized in that it comprises at least the detection, from a sample of nucleic acid extracted from peripheral blood mononuclear cells, of at least one heterozygous mutation of the MDR3 gene and/or of a homozygous mutation which does not destroy the expression of the protein expressed by said gene with phosphatidylcholine transporter activity, in adult individuals associating cholesterol microcholelithiasis and intrahepatic cholestasis.

For the purposes of the present invention, the expression "mutation which does not destroy the expression of the protein having phosphatidylcholine transporter activity" is intended to mean both mutations which lead to the expression of a protein having residual phosphatidyl transporter activity and mutations which decrease the level of expression of the normal protein (mutation in the promoter for example). These various mutations do not induce any hepatobiliary symptoms in children, but the appearance, in young adults, of symptoms associating cholesterol microcholelithiasis and intrahepatic cholestatis, induced by additional factors linked to the host and/or to the environment.

In accordance with the invention, said MDR3 gene mutation is located in at least one of the following exons: 4, 5, 6, 8, 9, 10, 12, 14, 15, 16, 17, 18, 19, 23 and/or 26.

More specifically:

in one aspect of the invention, said mutation is preferably located in exon 6 and/or in exon 9 and/or in exon 12.

in another aspect of the invention, said mutation is preferably located in exons 9, 10, 12, 14, 15, 17 or 18; indeed, as it emerges from the obtained data, most mutations are localized in the central part of the molecule, close to nucleotide binding domain 1 (NBD1), or in adjacent transmembrane domains and intracellular loops (see FIGS. 1 and 2). More precisely, 80% of mutations are situated in regions encoded by exons 9 to 18, which correspond approximately to 38% of the encoding region (TM5 and 6; $3^{rd}$ intracellular loop including NBD1; TM7 and 8).

all the detected mutations (point mutations or other type of mutations such as SNPs) are significantly related to LPAC, when, based on a multivariate analysis (see example 3), able to define a clinical score, said score being $\geq 2$ (1 point if age at the onset of symptoms was below 40 years, 1 point for recurrence after cholecystectomy and 1 point for the presence of intrahepatic spots).

According to an advantageous embodiment of said method, it comprises the detection of a mutation selected from the group consisting of:

a mutation in exon 4 at nucleotide 175,
a mutation in exon 6 at nucleotide 495, 504 or 523,
a mutation in exon 8 at nucleotide 711,
a mutation in exon 9 at nucleotide 902 or 959,
a mutation in exon 10 at nucleotides 1007-1015 (insertion or deletion)
a mutation in exon 12 at nucleotide 1327,
a mutation in exon 14 at nucleotide 1584,
a mutation in exon 15 at nucleotide 1772,
a mutation in exon 16 at nucleotide 1954,
a mutation in exon 17 at nucleotide 1973,
a mutation in exon 18 at nucleotides 2270-2273 (insertion)
a mutation in exon 19 at nucleotide 2363,
a mutation in exon 23 at nucleotide 2800 and
a mutation in exon 26 at nucleotide 3481.

More specifically, said method comprises the detection of a mutation selected from the group consisting of:

a heterozygous missense mutation in exon 6 at nucleotide 523:T/C (TCG/CCG), leading to the amino acid mutation T175A; this amino acid is located in a conserved amino acid sequence required for the ATPase activity of the MDR3 protein, a homozygous missense mutation in exon 9: at nucleotide 959: C/T(TCC/TTC), leading to the amino acid mutation S320F, which is located at the end of transmembrane domain 5 (TM5), and a heterozygous mutation in exon 12: insertion of an adenine at nucleotide 1327 (1327insA) in the first nucleotide-binding domain (NBD1); this mutation causes a reading frame shift at codon 443 and the appearance of a stop codon (nt 1339-1341), leading to the expression of a 446 amino acid truncated protein.

These MDR3 gene mutations and others in patients with LPAC syndrome are summed up in the following Tables I and II:

TABLE I

MDR3 gene point mutations in patient with LPAC syndrome

| Gene Position | Location and nucleotide change | Peptide change | Protein domain | Status |
|---|---|---|---|---|
| 6 | 495T→A | Phe 165 Ile | $1^{st}$ intracellular loop | Hetero |
|  | 523A→G | Thr 175 Ala | between TMA-TM3 | Hetero |
| 9 | 902T→C | Met 301 Thr | TM5 | Hetero |
|  | 959C→T | Ser 320 Phe |  | Homo |
| 10 | 1007-1015insT | 355 stop | TM6 | Hetero |
|  | 1007-1015delT | 341 stop | TM6 | Hetero |
| 12 | 1327insA | 447 stop | Close to NBD1$_1$ | Hetero |
| 14 | 1584G→C | Glu 528 Asp | Close to NBD1$_1$ | Hetero |
| 15 | 1772T→A | Leu 591 Gln | $3^{rd}$ intracellular loop | Homo |
| 17 | 1973G→A | Try 658 Stop | $3^{rd}$ intracellular loop linker domain | Hetero |
| 18 | 2270-2273insT | 793 Stop | $4^{th}$ intracellular loop between TM8-TM9 | Hetero |
| 19 | 2363G→T | Arg 788 Glu | $4^{th}$ intracellular loop between TM8-TM9 | Hetero |
| 23 | 2800G→T | Ala 934 Thr | $5^{th}$ intracellular loop between TM10-TM11 | Homo |
| 26 | 3481C→T | Pro 1161 Se | Close to NBD2 | Hetero |

Note:
The A of ATG of the initiator Met codon was denoted as "nucleotide +1"

Said Table II indicates the most frequent allele to total number of allele ratio for each tested SNPs in the different groups of patients. Nucleotide changes in SNPs are underlined.

Note: The A of ATG of the initiator Met codon was denoted as "nucleotide +1"

Thus five single-nucleotide polymorphisms (SNPs) in the coding region of the MDR3 gene may be identified in LPAC patients besides the point mutations described here above in Table I. In all cases, a high score (as defined here above), i.e. ≧2 is obtained.

According to another advantageous embodiment of the method according to the invention, it comprises:

a first step of amplification of a nucleic acid fragment, in which at least one of said mutations is liable to be observed, from the nucleic acid extracted from peripheral blood mononuclear cells, using at least one primer selected from the group consisting of the primers represented in the attached sequence listing under the numbers SEQ ID NO:1 to SEQ ID NO:13 or in the hereafter Table III under the numbers SEQ NO:15 to SEQ ID NO:66, and a second step of detection of the presence of at least one of said mutations, using said amplification fragment(s) obtained.

TABLE III

Intronic primers for amplifying the different exons of MDR3 gene.

| Name (SEQ ID NO:) | SEQUENCE |
|---|---|
| MDR3-SENS2 (SEQ ID NO: 15) | GGAGAGGGTGTACTTGG |
| MDR3-AS2 (SEQ ID NO: 16) | AGGCATCAACCGATTTTTAC |
| MDR3-SENS3 (SEQ ID NO: 17) | CTTTGTAGTACCTTCGACAG |

TABLE II

Characterization of MDR3 gene SNPs and determination of the main allele frequency in patients with and without LPAC syndrome and in control subjects.

| SNP Localization | Exon 4 | Exon 5 | Exon 6 | Exon 8 | Exon 16 |
|---|---|---|---|---|---|
| Nucleotide Change | 175 C→T | 342 T→C | 504 T→C | 711 A→T | 1954 A→G |
| Amino Acid | Leu 59 | Thr 114 | Asn 168 | Ile 237 | Arg 652 Gly |
| Most frequent allele | C_TG | AC_T | AA_C | AT_A | A_GG |
| Mutation LPAC Phenotype (Score ≧2) | 21/24 (87.5%) | 24/24 (100%) | 16/30 (53.3%) | 21/24 (87.5%) | 23/24 (95.8%) |
| No mutation LPCA phenotype (Score ≧2 | 27/28 (96.4%) | 27/28 (96.4%) | 3/28 (10.7%) | 27/28 (96.4%) | 27/28 (96.4%) |
| No mutation No LPAC phenotype (Score <2) | 52/56 (92.8%) | 56/56 (100%) | 29/56 (51.8%) | 51/56 (91.1%) | 51/56 (91.1%) |
| Control subjects | 54/66 (81.8%) | 65/66 (98.5%) | 36/66 (54.5%) | 50/66 (89.3%) | 61/66 (92.4%) |
| Bonferroni Adjusted P-value (5 comparisons) | 0.05 | 0.99 | 0.001 | 0.14 | 0.99 |

TABLE III-continued

Intronic primers for amplifying the different exons of MDR3 gene.

| Name (SEQ ID NO:) | SEQUENCE |
|---|---|
| MDR3-AS3 (SEQ ID NO: 18) | TTGTGCTCAAGCAACCCTCC |
| MDR3-SENS4 (SEQ ID NO: 19) | GAGGAGAAATTCCATTCCAC |
| MDR3-AS4 (SEQ ID NO: 20) | CAACTCCCAAATTTTTACCC |
| MDR3-SENS5 (SEQ ID NO: 21) | TAAAAACCTGGCAATGCC |
| MDR3-AS5 (SEQ ID NO: 22) | AACTCTGTAATTGGAAATTATC |
| MDR3-SENS6 (SEQ ID NO: 23) | CCATCATGGAGCTCATCACTT |
| MDR3-AS6 (SEQ ID NO: 24) | GCTGCCAGATGATCGATTTC |
| MDR3-SENS7 (SEQ ID NO: 25) | GTTTGTTGGATGTCTACTTC |
| MDR3-AS7 (SEQ ID NO: 26) | CCTGAACAGGTACAAGTACG |
| MDR3-SENS8 (SEQ ID NO: 27) | GTGCCTTTAAACTTTTCTCC |
| MDR3-AS8 (SEQ ID NO: 28) | CGAGAAGGGTTAATATTAGG |
| MDR3-SENS9 (SEQ ID NO: 29) | GCCGAGTGTGACTCGGAC |
| MDR3-AS9 (SEQ ID NO: 30) | GGTCTAACCACATGCTATTTTC |
| MDR3-SENS10 (SEQ ID NO: 31) | CTATGTTACATATACATCAC |
| MDR3-AS10 (SEQ ID NO: 32) | GTACAACTTATTCAATGTAGTTG |
| MDR3-SENS11-12 (SEQ ID NO: 33) | GACATTCCAGGTCCTATTTTGG |
| MDR3-AS11-12 (SEQ ID NO: 34) | GCTTGGTTCTTCCCACTTAC |
| MDR3-SENS13 (SEQ ID NO: 35) | GGTAGGATGTTTTTCATG |
| MDR3-AS13 (SEQ ID NO: 36) | CCTTTGAAGAATAAACTCAG |
| MDR3-SENS14 (SEQ ID NO: 37) | GACAAAGCTCCATGTTGTC |
| MDR3-AS14 (SEQ ID NO: 38) | CTGTTTCTCAGCCCAGACTC |
| MDR3-SENS15 (SEQ ID NO: 39) | ATCCAAGTGCTTAACTGTG |
| MDR3-AS15 (SEQ ID NO: 40) | GTATAGCATTCACTGGATC |
| MDR3-SENS16 (SEQ ID NO: 41) | TACATCCATTTGGAGACAC |
| MDR3-AS16 (SEQ ID NO: 42) | GCAAGGCTAAGAATTTC |
| MDR3-SENS17 (SEQ ID NO: 43) | GCCTTTTCTATGTCTACAG |
| MDR3-AS17 (SEQ ID NO: 44) | AGAAGCAGCAGCTGATG |
| MDR3-SENS18 (SEQ ID NO: 45) | CTCAAGCCACTATTTATGAG |
| MDR3-AS18 (SEQ ID NO: 46) | AGAATTTGGAAGCTCCATTAG |
| MDR3-SENS19 (SEQ ID NO: 47) | CAACTCATAACTTTGCTAC |
| MDR3-AS19 (SEQ ID NO: 48) | CATGCATATCGACATAACAATAAG |
| MDR3-SENS20 (SEQ ID NO: 49) | GGTCTCCCCTAAATTTCCTC |
| MDR3-AS20 (SEQ ID NO: 50) | CAAGTGTGGGTATGCTACATG |
| MDR3-SENS21 (SEQ ID NO: 51) | GCTGGAGCGCATGCATTTG |
| MDR3-AS21 (SEQ ID NO: 52) | GTTGTAGTGGGCACAAA |
| MDR3-SENS22 (SEQ ID NO: 53) | CTTGAACAGATTATGCCTTTGG |
| MDR3-AS22 (SEQ ID NO: 54) | TCCTAGTCACATCAAAAAGC |
| MDR3-SENS23 (SEQ ID NO: 55) | CTTAAACCCACTCGGCC |
| MDR3-AS23 (SEQ ID NO: 56) | CACAGGAGTCATTTTTTTCCTAC |
| MDR3-SENS24 (SEQ ID NO: 57) | GACTTTCAAACATCATGGAG |
| MDR3-AS24 (SEQ ID NO: 58) | CTTATCCTGTAGCTATAATC |
| MDR3-SENS25 (SEQ ID NO: 59) | CTGGCACCAGAACTATACC |
| MDR3-AS25 (SEQ ID NO: 60) | ATTATGACAATATTGGTTGGGC |
| MDR3-SENS26 (SEQ ID NO: 61) | GAAGCTGCTGACACCC |
| MDR3-AS26 (SEQ ID NO: 62) | GAAGTGCCTTGTCCAAGTTG |
| MDR3-SENS27 (SEQ ID NO: 63) | AATAGAACTGTCAACTGTTAAGC |
| MDR3-AS27 (SEQ ID NO: 64) | TTTTCCCCCTGTGCTTG |
| MDR3-SENS28 (SEQ ID NO: 65) | GATTAGAAAGGTAACATTTTC |
| MDR3-AS28 (SEQ ID NO: 66) | GGGTCTTCTAAATTGATC |

According to the invention, said nucleic acid fragment on which the amplification is performed is selected from the group which consists in mRNA, cDNA and genomic DNA.

According to an advantageous arrangement of this embodiment of the method, the first amplification step consists of direct PCR amplification of at least one of exons 6, 9 and 12 of the genomic DNA with the following primers, located in the flanking intronic regions:

primers SEQ ID NO:1 and SEQ ID NO:2, which make it possible to amplify a 321 pb fragment covering exon 6,
primers SEQ ID NO:3 and SEQ ID NO:4, which make it possible to amplify a 210 pb fragment covering exon 9, and
primers SEQ ID NO:5 and SEQ ID NO:6, which make it possible to amplify a 154 pb fragment covering exon 12.

According to another advantageous arrangement of this embodiment of the method, the first amplification step consists of RT-PCR amplification of the mRNAs by two overlapping PCRs, using two pairs of primers, selected from the group consisting of the following pairs:

first pair: SEQ ID NO:7 and SEQ ID NO:8
second pair:
SEQ ID NO:9 and SEQ ID NO:10
SEQ ID NO:11 and SEQ ID NO:10
SEQ ID NO:12 and SEQ ID NO:10, and
SEQ ID NO:13 and SEQ ID NO:10.

More specifically, for the detection from the mRNA, the method according to the invention advantageously comprises:

a first PCR amplification of 2100 pb fragment (fragment 1) corresponding to exons 1 to 16 of the human MDR3 gene, with the pair of primers:

```
5'-CCTGCCAGACACGCGCGAGGTTC-3'      (SEQ ID NO: 7)
and

5'-CTTCAAGTCCATCGGTTTCCACATC-3',   (SEQ ID NO: 8)
and
``` a second amplification of fragment 1, using various pairs of primers, capable respectively of amplifying a fragment comprising exon 6, a fragment comprising exon 9 and a fragment comprising exon 12.

Even more specifically:

a 1746 pb fragment (fragment 2) comprising exon 6 is amplified with the following pair of primers:

```
5'-CCTTGTCGCTGCTAAATCC-3'          (SEQ ID NO: 9)
and

5'-GGCTCTTCTGACACATTTGTG-3';       (SEQ ID NO: 10)
``` a 1483 pb fragment (fragment 3) comprising exon 9 is amplified with the following pair of primers:

```
                            (SEQ ID NO: 11) and SEQ ID NO: 10
5'-GGAATTGGTGACAAGGTTGG-3';
``` a 1162 pb fragment (fragment 4) comprising exon 9 is amplified with the following pair of primers:

```
                            (SEQ ID NO: 12) and SEQ ID NO: 10
5'-GCTATTTCAGCAAACATTTCCATGG-3';
``` an 823 pb fragment (fragment 5) comprising exon 12 is amplified with the following pair of primers:

```
                            (SEQ ID NO: 13) and SEQ ID NO: 10
5'-GCTAACGTCAAGATCTTGAAGG-3'.
```

According to another advantageous arrangement of this embodiment of the method, the first amplification step consists of direct PCR amplification of at least one of exons 6, 9, 10, 12, 14, 15, 17, 18, 19, 23, and 26 and further of at least one of exons 4, 5, 8 and/or 16 of the genomic DNA with the primers, located in the flanking intronic regions, as specified in the hereabove Table III (SEQ ID NO:15 to 66).

According to yet another advantageous arrangement of this embodiment of the method, the second step of detection of the presence of at least one of said mutations using the amplified fragment is carried out, as appropriate, using one of the following methods:

sequencing
enzyme restriction or
techniques of the PCR/PCR/LDR reaction.

When the mutation results in the appearance or disappearance of a restriction site in the amplified fragment, the mutations are detected by digestion with the enzyme recognizing said restriction site, compared with a control which does not exhibit said mutation.

For example:

digestion of the 210 pb amplification fragment as defined above with the HinfI enzyme: detection of a 210 pb fragment corresponds to the presence of wild-type allele, whereas detection of two fragments (142 pb and 48 pb) corresponds to the presence of the mutated allele;
digestion of the 210 pb amplification fragment as defined above with the BamHI enzyme: detection of a 210 pb fragment corresponds to the presence of the mutated allele and detection of two fragments corresponds to the presence of the wild-type allele.

When the mutation cannot be detected by enzyme digestion, the fragment amplified by PCR is sequenced according to conventional techniques; by way of example, mention may be made of the dideoxynucleotide technique.

When the mutation to be detected corresponds to the insertion or to the deletion of a small sequence, said mutation can be detected using techniques of the PCR/PCR/LDR type, which are based on detecting the ligation of allele-specific primers using a thermostable ligase (Favis et al., Nature Biotech., 2000, 18, 561-564).

Such a method may advantageously be used to evaluate the risk of appearance of a syndrome associating intrahepatic cholestasis and cholesterol micro-cholelithiasis in families at risk of cholesterol lithiasis and/or having unexplained hepatic biological abnormalities.

When a mutation, as defined above, is detected in individuals at risk, said evaluation method can advantageously also comprise searching for intrahepatic microcrystals of cholesterol, measuring the cholesterol saturation index of the bile, determining the cholesterol/bile phospholipids ratio, assaying bile phospholipids, and testing against ursodeoxycholic acid.

The diagnosis may be considered to be positive for the abovementioned syndrome when one of the abovementioned mutations is screened, associated with the presence of microcholelithiasis, a very low level of bile phospholipids and a cholesterol saturation index of the bile of greater than 1.

Another subject-matter of the present invention is also the use of the various primers as defined above, for the screening of a syndrome associating (i) intrahepatic hyperechoic foci with or without intrahepatic sludge or microlithiasis and further on cholesterol microcholelithiasis, intrahepatic cholestasis and (ii) at least one mutation of the MDR3 gene.

Another subject-matter of the present invention is also a kit for the screening of a syndrome associating (i) intrahepatic hyperechoic foci with or without intrahepatic sludge or microlithiasis and further on cholesterol microcholelithiasis, intrahepatic cholestasis and (ii) at least one mutation of the MDR3 gene, characterized in that it comprises at least two primers as defined above, capable of detecting a mutation of the human MDR3 gene, as defined above.

Another subject-matter of the present invention is also a kit for evaluating the risk of appearance of a syndrome associating (i) intrahepatic hyperechoic foci with or without intrahepatic sludge or microlithiasis and further on cholesterol microcholelithiasis, intrahepatic cholestasis and (ii) at least one mutation of the MDR3 gene, in a population at risk, characterized in that it comprises, besides the primers capable of detecting the mutation of the MDR3 gene as defined above, reagents for assaying cholesterol and bile phospholipids.

Preferably, the reagents are enzymatic reagents.

Another subject-matter of the present invention is also the use of ursodeoxycholic acid for preparing a medicinal product intended to treat a hepatic syndrome associating (i) intrahepatic hyperechoic foci with or without intrahepatic sludge or microlithiasis and further on a cholesterol microcholelithiasis, intrahepatic cholestasis and (ii) at least one mutation of the MDR3 gene.

BRIEF DESCRIPTION OF DRAWINGS

Besides the above arrangements, the invention also comprises other arrangements which will emerge from the following text, which refers to examples of implementation of the present invention and also to the attached drawings in which.

EXAMPLE 1

Materials and Methods

Figure 1:
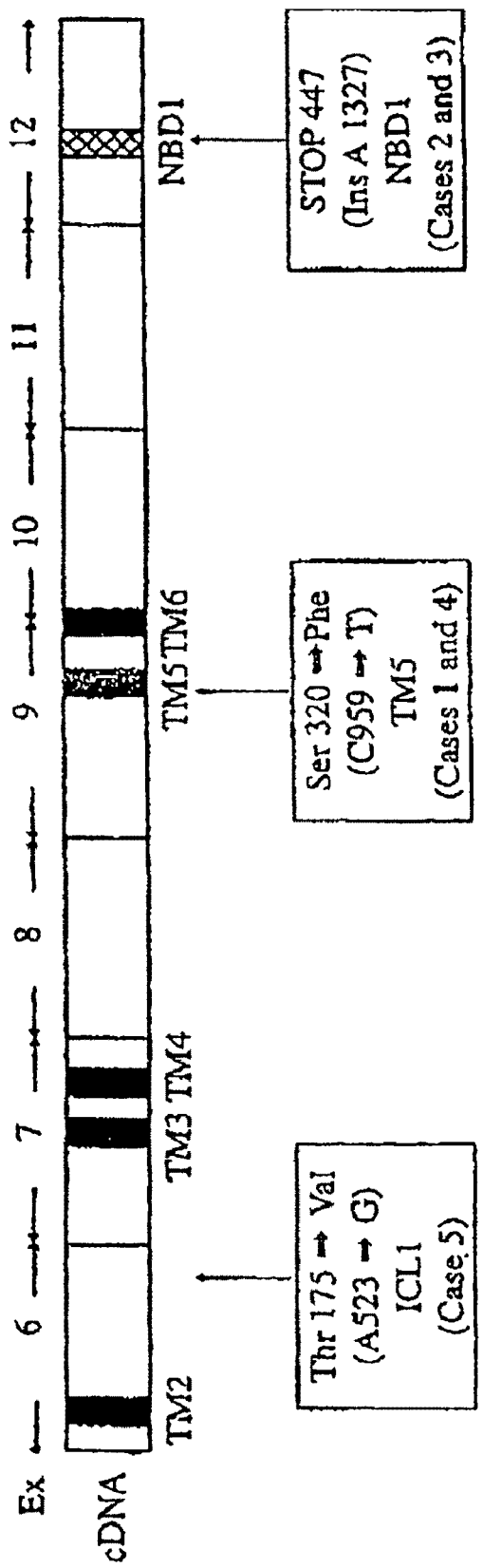
FIG. 1 illustrates the location of the various mutations on the cDNA encoding the MDR3 protein. Exons (Ex) 6 to 12 are represented by white boxes, the black boxes correspond to transmembrane domains (TM) 2 to 6 and the hashed box represents the nucleotide-binding domain (NBD1). The location of the various mutations is represented by arrows. ICL1 corresponds to the intracellular loop of the MDR3 protein, which is essential for the ATPase activity of this protein.
Figure 2:
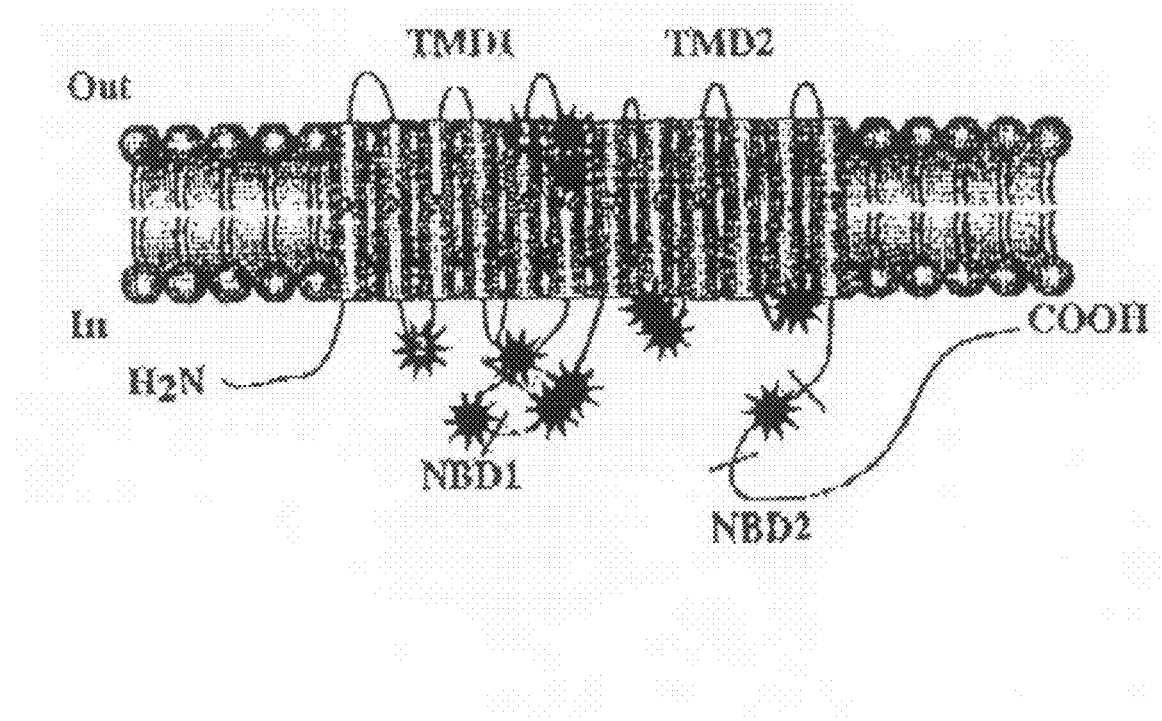
FIG. 2 illustrates the localization of the mutations in the different domains of the MDR3 protein. The gray boxes correspond to the transmembrane domains of the protein. TMD1 and 2 correspond to the two symmetrical regions containing the TM domains 1-6 and 7-12, respectively. NBD 1 and 2 correspond to the nucleotide binding domains and the black stars correspond to the mutations that have been identified in patients presenting LPAC. The figures in the stars indicate the number of patients having the corresponding mutation.

1—Characteristics of the Patients Included in the Study

Six patients with no family history of PFIC were studied: five women (patients 1, 2, 4, 5 and 6) and one man (patient 3). They exhibit: chronic intrahepatic cholestasis, cholesterol cholelithiasis, intrahepatic microcholelithiasis as attested by echography and an abnormality of the MDR3 gene; treatment with ursodeoxycholic acid (UDCA) leads to complete disappearance of the symptoms and standardizing of the enzymatic constants of the liver. In the five women, this syndrome appeared during pregnancy or after treatment with oral contraceptives.

Analysis of the bile shows: an oversaturation of cholesterol, a low phospholipid level and the presence of cholesterol crystals.

2—Preparation of DNA and RNA

Circulating blood mononuclear cells are isolated by centrifugation (Histopaque-1119, Sigma Diagnostics). The DNA is extracted from $5 \times 10^6$ lymphocytes using the QIAamp kit (Qiagen-GmbH, Germany). The total RNA is extracted from $5 \times 10^6$ peripheral blood nuclear cells (kit from Eurobio, les Ulis, France) in accordance with the manufacturer's instructions. The RNA and DNA concentrations are quantified by spectrophotometry.

3—Amplification of the MDR Gene Transcripts by RT-PCR

A reverse transcription is carried out in a reaction volume of 20 µl containing 500 mM of dNTP, 10 mM of DTT, 0.5 U.ml$^{-1}$ of RNasine (Madison, Wis.), 5 mM of random hexamers and 10 µg.ml$^{-1}$ of reverse transcriptase (Gibco BRL, Bethesda, Md.). The RNA extracts are heated for 5 minutes at 70° C. and cooled on ice before being added (1 µg) to the reaction mixture and incubated for one hour at 37° C.

The cDNA obtained (5 µl, 0.25 µg) is amplified by the PCR method using synthetic oligonucleotide primers (Genosys, Cambridge, UK). A first PCR, producing the 2100 pb fragment 1, is carried out in a reaction medium of 25 µl containing 10 mM of Tris-HCl, pH 8.3, 1.5 mM of magnesium chloride, 0.001% of gelatin, 0.05 U of Taq DNA polymerase, 350 µM of each dNTP and 0.5 µM of each primer (sense and antisense) as defined in Table IV below:

TABLE IV

Sequence of the primers and size of the fragments obtained by RT-PCR amplification of the MDR3 gene

| Fragment | Pairs of PCR primers (5'→3') | | Position | Position (exon) | Product size (pb) |
|---|---|---|---|---|---|
| 1 | CCTGCCAGACACGCGCGAGGTTC | (SEQ ID NO: 7) | 32-2078 | (1-16) | 2100 |
|   | CTTCAAGTCCATCGGTTTCCACATC | (SEQ ID NO: 8) | | | |
| 2 | CCTTGTCGCTGCTAAATCC | (SEQ ID NO: 9) | 296-2041 | (5-16) | 1746 |
|   | GGCTCTTCTGACACATTTGTG | (SEQ ID NO: 10) | | | |
| 3 | GGAATTGGTGACAAGGTTGG | (SEQ ID NO: 11) | 559-2041 | (9-16) | 1483 |
|   | GGCTCTTCTGACACATTTGTG | (SEQ ID NO: 10) | | | |
| 4 | GCTATTTCAGCAAACATTTCCATGG | (SEQ ID NO: 12) | 880-2041 | (9-16) | 1162 |
|   | GGCTCTTCTGACACATTTGTG | (SEQ ID NO: 10) | | | |

TABLE IV-continued

Sequence of the primers and size of the fragments obtained by RT-PCR amplification of the MDR3 gene

| Fragment | Pairs of PCR primers (5'→3') | | Position | Position (exon) | Product size (pb) |
|---|---|---|---|---|---|
| 5 | GCTAACGTCAAGATCTTGAAGG | (SEQ ID NO: 13) | 1219-2041 | (11-16) | 823 |
|   | GGCTCTTCTGACACATTTGTG | (SEQ ID NO: 10) | | | |
| 6 | GAGGCCAACGCCTATGAG | (SEQ ID NO: 14) | 1522-2041 | (13-16) | 520 |
|   | GGCTCTTCTGACACATTTGTG | (SEQ ID NO: 10) | | | |

The pair of primers for the amplification of fragment 1 has already been described (J M. De Vree et al., mentioned above).

The primary PCR amplification is carried out under the following conditions: an initial denaturation step at 94° C. for five minutes is followed by 35 cycles alternating a denaturation step at 94° C. for thirty seconds, a primer hybridization step at 68° C. for thirty seconds, and an extension step at 72° C. for two minutes.

Overlapping PCRs producing five overlapping fragments (fragments 2, 3, 4, 5 and 6) are carried out by adding 2 µl of the amplification product of the primary PCR to a secondary PCR reaction mixture (50 µl). The reaction medium is identical to that described above (for the primers, see Table IV).

The secondary PCR amplification is carried out under the following conditions: an initial denaturation step at 94° C. for five minutes is followed by 35 cycles alternating a denaturation step at 94° C. for thirty seconds, a primer hybridization step at 60° C. for thirty seconds, and the extension step at 72° C. for 90 seconds.

Negative controls are carried out on RNA samples amplified in the absence of reverse transcriptase. The amplification products are separated by electrophoresis in a 1.5% agarose gel containing ethidium bromide. The amplified DNA fragments are visualized under an ultraviolet lamp.

4—PCR Amplification of Exons 6, 7, 9 and 12 of the MDR3 Gene

Exons 6, 9 and 12 are amplified by PCR using primers located in the flanking intronic regions and using genomic DNA as matrix:

a 321 pb fragment covering exon 6 is amplified using the following primers:
sense primer 5'-CTACTCAGGATTGGGTGCTGG-3' (SEQ ID NO: 1) and
antisense primer 5'-GCTAGAACATGGCTGCCAG-3' (SEQ ID NO: 2);
a 210 pb fragment covering exon 9 is amplified using the following primers:
sense primer 5-CCCTCTCATTTTTCTGGTAG-3' (SEQ ID NO: 3) and
antisense primer 5'-GTTAGGAGAACTACTTACTG-3' (SEQ ID NO: 4);
a 154 pb fragment covering exon 12 is amplified using the following primers:
sense primer 5'-CCTTACAGATCTTGAAGGGC-3' (SEQ ID NO: 5) and
antisense primer 5'-GCTTGGTTCTTCCCACTTAC-3' (SEQ ID NO: 6).

The PCR reaction is carried out in a final volume of 50 µl, in the presence of 100 ng of genomic DNA and of 1.5 mM of $MgCl_2$. The primer hybridization step is carried out at 60° C. (exon 7), 50° C. (exon 9) and 56° C. (exon 12), and the other steps are identical to those set out above for the cDNA, with the exception of the number of cycles (30 instead of 35). The amplification products are separated by electrophoresis in a 2% agarose gel containing ethidium bromide. The amplified DNA fragments are visualized under an ultraviolet lamp.

5—Analysis of Mutations

The amplification products are sequenced (dideoxyterminator kit) in accordance with the manufacturer's (Perkin-Elmer) instructions. The sequencing reactions are carried out in a Perkin-Elmer thermocycler 9600 using the same primers as for the amplification of the exons (see 4-). The extension products are separated from the nonincorporated nucleotides and from the primers by column centrifugation (quick spin TM, Boehringer Mannheim), and they are then dried and resuspended in 4 µl of deionized formamide containing 50 mM of EDTA, pH8. These products are then heated for 2 minutes at 90° C., transferred onto ice and immediately loaded onto a denaturing 6% polyacrylamide gel. The migration is carried out at 30 W for 12 h (automated DNA sequencer, model ABI 373 A).

6—Restriction Analysis

The exon-9 amplification fragments are digested (15 µl) for 6 hours at 37° C. with Hinf I or BamH I (2 IU, Biolabs), and the fragments obtained are visualized on 2% agarose gel.

7—Bile Composition

A polarized light microscope is used to detect the presence of cholesterol crystals in samples of fresh bile.

The concentration of total bile salts is measured by an enzymatic technique using 3α-hydroxysteroid dehydrogenase (Enzabile, Nycomed, Oslo, Norway). The content of total phospholipids is determined by an enzymatic method in the presence of phospholipase D and choline oxidase. The cholesterol is determined by an enzymatic reaction with cholesterol oxidase or cholesterol esterase. The cholesterol saturation indices for the hepatic bile samples are calculated from Carey's critical tables (J. Lipid Res., 1978, 19, 945-955).

EXAMPLE 2

Results

The six patients mentioned above were studied.

1—Morphology and Histopathology

Ultrasonography (US) makes it possible to detect multiple microcalculi in the intrahepatic bile ducts in the six patients.

A liver biopsy sample obtained in patients 3 and 4 shows moderate portal inflammation and proliferation of the bile ducts without any damage to said ducts. Extensive fibrosis is also observed in patient 4.

As regards patient 3, many biliary microcalculi visible on the X-ray were extracted from the intrahepatic and extrahepatic bile ducts. Biochemical analysis of these calculi show that they consist essentially of cholesterol.

A cholangiography was performed in patient 5, and shows localized sclerozing cholangitis characterized by irregular left intrahepatic bile ducts exhibiting alternating regions of stenosis and regions of saccular dilation.

2—Composition of the Hepatic Bile

The bile lipid composition of the hepatic bile was studied using samples obtained by radioscopy of the duodenum (patients 2 and 3) or using a T tube (patients 5 and 6). The results obtained in the untreated patients or the patients receiving treatment with UDCA are given respectively in Tables V and VI below.

TABLE V

Bile lipid composition of the hepatic bile from untreated patients

| Parameters measured | Normal values* | Case 2 | Case 5 | Case 6 |
|---|---|---|---|---|
| Bile lipid classes (mol %) | | | | |
| Bile salts (BS) | 72.6 | 72.1 | 57.3 | 94.2 |
| Phospholipids (PL) | 20.6 | 18.7 | 25.3 | 1.4 |
| Cholesterol (CH) | 7.8 | 9.1 | 17.4 | 4.5 |
| Cholesterol saturation index (CSI) | 1.1 | 1.98 | 20.9 | ND |
| Lipid ratios | | | | |
| CH/PL | 0.38 | 0.49 | 0.70 | 3.21 |
| PL/BS | 0.29 | 0.26 | 0.44 | 0.01 |
| CH/BS | 0.10 | 0.13 | 0.30 | 0.05 |
| Concentration of bile PL | 15.6 | 6.39 | 1.77 | 0.30 |

*The normal values are derived from Lamont et al., (Progress in Liver Diseases, Boyer et al. Ed., W. B. Saunders Company, Philadelphia, 1992, 165-191).

TABLE VI

Bile lipid composition of the hepatic bile from patients receiving treatment with UDCA

| Parameters measured | Normal values* | Case 5 | Case 6 |
|---|---|---|---|
| Bile lipid classes (mol %) | | | |
| Bile salts (BS) | 72.6 | 47.5 | 72 |
| Phospholipids (PL) | 20.6 | 35.7 | 19.7 |
| Cholesterol (CH) | 7.8 | 16.8 | 8.2 |
| Cholesterol saturation index (CSI) | 1.1 | 4.0 | 1.8 |
| Lipid ratios | | | |
| CH/PL | 0.38 | 0.47 | 0.42 |
| PL/BS | 0.29 | 0.75 | 0.27 |
| CH/BS | 0.10 | 0.35 | 0.11 |
| Concentration of bile PL | 15.6 | 7.77 | 6.03 |

*The normal values are derived from Lamont et al. (mentioned above).

Analysis of the bile samples by microscopy shows the presence of many cholesterol monohydrate crystals.

All the freshly taken bile samples derived from patients not treated with UDCA have the following three characteristics:

1°) a high cholesterol saturation index (CSI),

2°) a high cholesterol/phospholipid (CH/PL) ratio, and

3°) a low or a very low concentration of phospholipids (PL), in comparison with the normal concentrations described (Lee et al., 1986, Gastroenterology, 90, 677-686; Lamont et al., mentioned above).

In patient 5, the large increase in the cholesterol/bile salts (CH/BS) ratio indicates that hypersecretion of cholesterol is responsible for the increase in the cholesterol saturation of the bile.

In patient 6, the large decrease in the phospholipids/bile salts (PL/BS) and cholesterol/bile salts (CH/BS) ratios indicates that, in this case, it is a decrease in the secretion of bile salts which is responsible for the increase in the cholesterol saturation of the bile.

After treatment with UDCA, a large decrease in the cholesterol saturation index is observed (patients 5 and 6), associated with an increase in the phospholipid concentration of the bile. Consequently, a decrease in cholesterol/bile salts ratio is observed in patient 5, whereas the low values for the cholesterol/bile salts and phospholipids/bile salts ratios become normal again in patient 6.

3—Analysis of the Mutations of the MDR3 Gene

The sequence of fragments 2, 3, 4, 5 and 6 obtained by RT-PCR was analyzed, and the mutations observed are as follows:

Insertion

In patients 2 and 3, the insertion of a single nucleotide in position 1327 of exon 12 is detected, in the form of a heterozygous mutation. This mutation leads to a modification of the open reading frame at codon 443, which leads to the appearance of a premature stop codon and the production of a 446 amino acid truncated protein.

Missense Mutation

A missense mutation at codon 320 of exon 9 ($Ser_{320}$ (TCC)→$Phe_{320}$(TTC), nucleotide 959 T→C) is present in the homozygous state in independent affected individuals derived from non-blood-related families (patients 1 and 4). However, the unaffected individuals of these two families are heterozygous for this substitution. This mutation is not detected on either of the alleles of the 63 independent controls (126 chromosomes), which demonstrates that this mutation does not correspond to a polymorphism of the MDR3 gene.

A missense mutation at codon 175 of exon 6 ($Thr_{175}$ (ACG)→$Ala_{175}$ (GCG), nucleotide 523 A→G) is present in the heterozygous state in patient 5. This mutation is not detected on either of the alleles of 51 independent controls (102 chromosomes), which demonstrates that this mutation does not correspond to a polymorphism of the MDR3 gene.

The sequencing of the fragments amplified from the genomic DNA confirms the homozygocity of patients 1 and 4 for the mutation S320F, the heterozygocity of patients 2 and 3 for the mutation 1327insA and the heterogocity of patient 5 for the mutation T175V.

Digestion of the amplified fragments with restriction enzymes confirms the presence of the mutation S320F in patient 1 (homozygous transition T→C) and in the members of the same family (heterozygous transition T→C), and also the absence of this mutation in normal nonrelated individuals.

No mutation was detected in exons 6, 9 and 12 of patient 6, who probably has a mutation in the promoter.

EXAMPLE 3

Second Study

Patients 32 patients, who were referred specifically for MDR3 gene analysis because of clinical history compatible with the syndrome that is described hereabove (e.g. having a symptomatic cholelithiasis with at least one of the following criteria: age at onset of symptoms less than 40, symptomatic cholelithiasis, recurrence after cholecystectomy, intraheptic hyperechoic foci with a topography compatible with lipid deposits along the luminal surface of the intrahepatic biliary tree with or without intrahepatic sludge or microlithiasis, familial history of cholelithiasis in 1$^{st}$ degree relatives, clinical history of intrahepatic cholestasis of pregnancy), were studied.

A second group of twenty-eight other patients presenting with a classic form of gallstone disease revealed by a single episode (or a second episode in one case) of typical biliary pain or cholecystitis that justified cholecystectomy constituted the control group. None of these patients had inflammatory biliary diseases (such as primary biliary cirrhosis, primary sclerosing cholangitis), fibrocystic liver disease (Caroli's disease), congenital hepatic fibrosis, Rendu-Osler, cystic fibrosis, protoporphyria, total parenteral nutrition, obesity (BMI≧30), biliary infection or infestation with parasites (including HIV infection), malabsorption (including ileal resection) and somatostatin synthetic analogs or hypocholesterolemic agent therapy, who were excluded by clinical examination and appropriate investigations including the results of anti-mitochondrial and anti-perinuclear antineutrophil cytoplasmic autoantibodies, ultrasonography, echoendoscopy, magnetic resonance cholangiography, T-tube cholangiography when a surgical treatment was performed, ERCP and, in few cases, liver biopsy. None of these patients had a medical history of progressive familial intrahepatic cholestasis during childhood and patients suffering from black pigment stones, hemolysis or cirrhosis were also excluded.

A third group comprises 33 consecutive patients without history of cholelithiasis and presenting with chronic cholestasis (primary biliary cirrhosis n=4, primary sclerosing cholangitis n=4), diverse acute or chronic liver diseases (chronic HBV or HCV hepatitis, non-alcoholic steatohepatitis (NASH), drug-induced hepatitis) (n=15) or a classic genetic hemochromatosis associated with C282Y homozygous mutation in the HFE gene (n=10) constituted a second control group. Based on previous data, the clinical feature characteristic of the syndrome were collected for the 60 patients with cholelithiasis as summed up in the following Table VII.

TABLE VII

| Patient characteristics | | |
|---|---|---|
| Patients (n) | 60 | |
| Age (years ± SD) | 38.1 ± 14.4 | |
| Gender (M/F) | 15/45 | |

| | (n) | (%) |
|---|---|---|
| Age at onset of symptoms <40 years | 37/60 | 62 |
| Symptomatic cholelithiasis | 60/60 | 100 |
| Recurrence after cholecystectomy | 28/60 | 47 |
| Cholecystectomy | 54/60 | 90 |
| Intrahepatic hyperechoic foci * | 32/60 | 53 |
| Medical history of ICP | 15/46 | 33 |
| Increased serum GGT activity ** | 22/60 | 37 |
| Familial history of cholelithiasis | 21/50 | 42 |
| Prophylactic UDCA treatment | 25/39 | 64 |

UDCA denotes ursodeoxycholic acid.
ICP denotes intrahepatic cholestasis of pregnancy.
* e.g. consisting intrahepatic hyperechoic foci with a topography compatible with lipid deposits along the luminal surface of the intrahepatic biliary tree with or without intrahepatic sludge or microlithiasis.
** at the time of genotype determination To determine the prevalence of the MDR3 mutations and single-nucleotide polymorphisms (SNPs), and the clinical factors predictive of these mutations in patients with symptomatic cholelithiasis, the entire MDR3 sequence in all 93 patients (see FIG. 3) was analysed. Written, informed consent was obtained from all participants.

Mutation Screening

Genomic DNA was obtained from peripheral white blood cells using standard procedures. We designed specific primers to amplify exons and splice junctions, using the Massachusetts Institute of Technology web site. The sequences of these intronic primers are those described in Table III.

Each PCR reaction contained 200 ng genomic DNA, with each primer at a concentration of 0.4 μM, 0.08 μM deoxynucleoside triphosphates (Pharmacia, Piscataway, N.J.), 1.5 mM magnesium chloride and 1.25 U Taq polymerase. PCR products were purified on sephadex column and sequenced using Big Dye Terminator Chemistry (Applied Biosystems). Identification and localization of MDR3 gene mutations and SNPs was assessed by sequence comparisons using Phred Phrap Consed Software.

Statistical Analysis

Fisher's exact test was used to compare proportions. All tests were at the 5% level, and reported P-values were two-sided. A multivariable, logistic regression model was used to select a set of clinical features predictive of a point mutation at the MDR3 locus. The multivariable model was selected by minimising the Akaike information criterion, a standard statistical procedure for selecting variables to be included as predictors (Burnham K. et al., Model selection and multimodel interference. NY, Springler Verlag, 2002). When comparing SNPs at the MDR3 locus, the first species risk was adjusted to the number of comparisons (=number of SNPs) according to the Bonferroni rule. All statistical analyses were performed using the R software (version 1.5.1) (Ihaka R. et al., J. Computational and Graphical Statistics, 1996, 5, 299-314).

Results

1. Clinical Phenotype Associated with MDR3 Gene Mutations

Table VIII: Unadjusted Odds-Ratio for the Presence of a Mutation at the MDR3 Locus in Cholelithiasis Patients

| Clinical Criteria | OR | CI 95% | P-value |
|---|---|---|---|
| Familial history of cholelithiasis in 1$^{st}$ degree relatives | 5.4 | [1.2, 29.4] | 0.01 |
| Increased serum GGT activity at the time of genotype determination | 1.1 | [0.3, 4.1] | 1 |
| History of ICP | 4.9 | [1.1, 24.0] | 0.02 |
| Intrahepatic hyperchoic foci | 12.4 | [2.4, 126.0] | 0.0005 |
| Recurrence after cholecystectomy | 18.9 | [3.6, 193.7] | <0.0001 |
| Age at onset of symptoms <40 | 7.8 | [1.5, 77.8] | 0.008 |
| Gender (Male vs Female) | 0.8 | [0.1, 3.4] | 1 |

Among the 32 patients suspected of having the syndrome, 18 (56%) presented a point mutation in the MDR3 gene while none of the 28 patients with a classical form of cholelithiasis and none of the 33 patients without cholelithiasis had mutation in this gene (p<0.001 and p<0.0001, respectively). For the whole population of 60 patients with symptomatic cholelithiasis, the unadjusted odds-ratios for the presence of a MDR3 gene mutation in this population are presented in Table VIII. Multivariate analysis showed that three independent factors were predictive of a mutation at the MDR3 locus: a recurrence of symptoms after cholecystectomy (adjusted OR=8.5), intrahepatic hyperechoic foci (adjusted OR=6.1), and age <40 years (adjusted OR=3.0).

Based on the multivariate analysis, a clinical score indicative of the presence of a MDR3 mutation was defined as follows: 1 point if age at the onset of symptoms was below 40 years, 1 point for recurrence after cholecystectomy and 1 point for the presence of intrahepatic spots.

All patients with a point mutation scored higher than 2 (mean ±SE: 2.7±0.5). By contrast, patients without point mutations had scored ranging from 0 to 3 (mean ±SE: 1.2±1.1) and could be divided into two groups (see FIG. 3): one group of patients scoring ≧2 (n=14) and another group scoring <2 (n=28). The score was therefore highly sensitive for the presence of a mutation (Se=100%, CI 95% [85%-100%]) but was not specific in this sample of patients (Sp=67%, CI 95% [52%-81%]).

2. Identification of MDR3 Gene Mutation in Patients with Cholelithiasis (Table 3)

Patients were screened for mutations in the MDR3 gene using PCR amplification and DNA sequencing of exons 2 to 28 and all splice junctions. 14 heterozygous and homozygous point mutation were identified amongst these 18 patients, all of them with a predictive score ≧2. None of these mutations was detected in a control panel of one hundred and forty chromosomes, thus demonstrating that they did not correspond to polymorphisms.

The mutations included as in example 2, three 1 bp-insertions and one 1 bp-deletion, resulting in a frameshift predicted to cause premature messenger RNA termination, a loss of protein function and ten single-nucleotide substitutions including one null mutation. Affected patients with heterozygous mutations exhibited 1 bp-insertion, 1 bp-deletion, nonsense mutations or missense mutations, while affected patients with homozygous mutations demonstrated only missense mutations. Most mutations were localized as mentioned here above in the central part of the molecule, close to nucleotide binding domain 1 (NBD1), or in adjacent transmembrane domains and intracellular loops (see FIG. 3). Eighty percent of mutations were indeed situated in regions encoded by exons 9 to 18, which corresponded approximately to 38% of the encoding region (TM 5 and 6; $3^{rd}$ intracellular loop including NBD1, TM 7 and 8).

Figure 3:
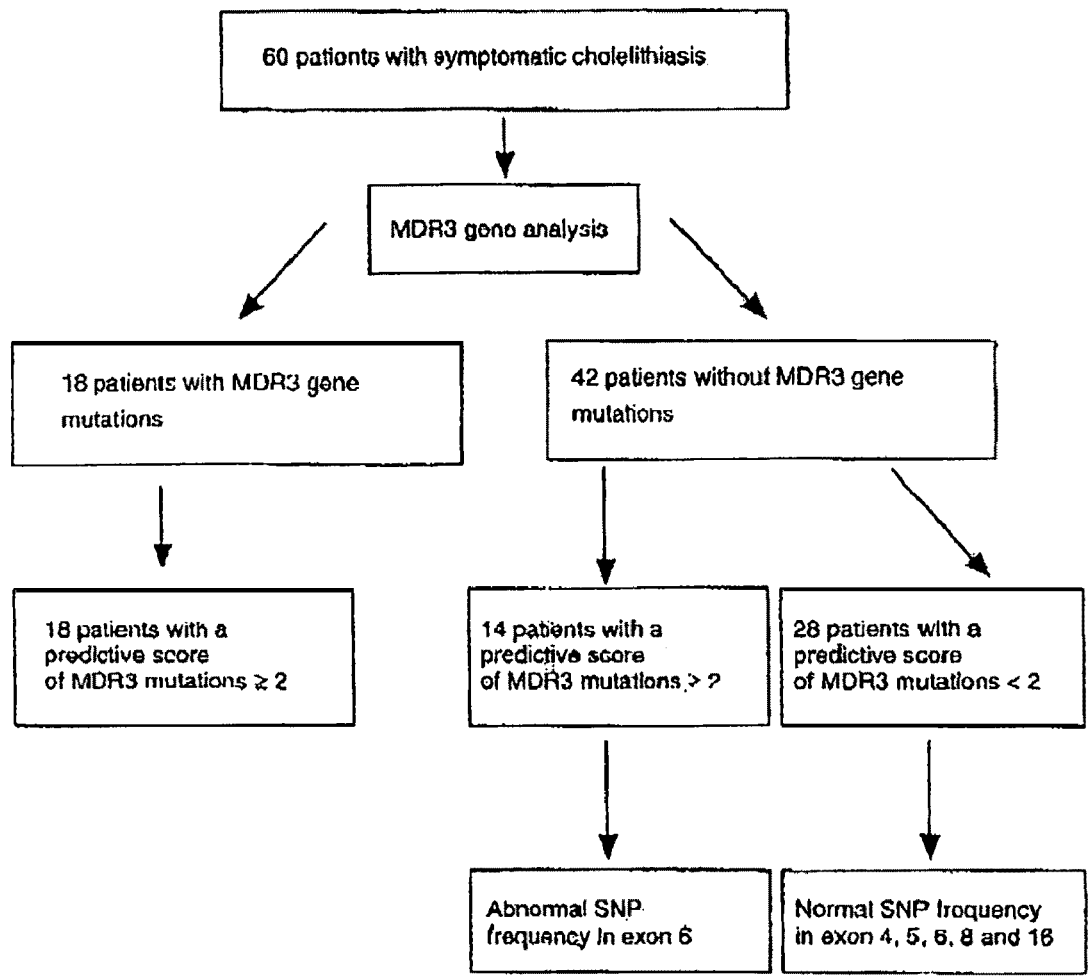
FIG. 3 illustrates as the study profile of example 3.

In contrast, no point mutations could be detected in 14 patients with a high score (≧2) and 28 patients with a low score (<2) (see FIG. 3). Furthermore, MDR3 gene sequence analysis in the 33 patients without cholelithiasis demonstrated two heterozygous missense mutations affecting non-conserved amino acids (Arg590Gln and Gly742Ser).

3. Identification of MDR3 Gene SNPs in Patients with Cholelithiasis (See Table II)

In order to search for a MDR3 defect even in patients with a high score but no point mutation, we investigated the frequency of MDR3 gene SNPs in these patients (see FIG. 3). The previously described Arg652Gly polymorphism was detected with a similar frequency (about 5%) in patients with and without MDR3 mutations and in control subjects (Jacquemin E. et al., Gastroenterology, 2001, 120, 1448-1458).

Five novel single-nucleotide polymorphisms (SNPs) in the coding region of the MDR3 gene have also been identified (see Table II here above). The allele frequency of the most frequent variant (e.g. 504 T→C, AAC) was only 10.7% in the group of LPAC syndrome patients with a high score but no MDR3 point mutations, while it reached 54.5% in control subjects, 51.8% in patients with cholelithiasis and a low score and 53.3% in patients with LPAC syndrome and MDR3 gene mutations (Bonferroni adjusted P-value <0.001). Other SNPs were more rare and were detected at similar frequencies in the different patient groups and in control subjects.

The mutation screening described in the invention method was unable to detect major DNA rearrangements, and nor did the analysis include the promoter or other potential regulation regions of the gene. Despite these limitations, the unexpected low frequency of the 504 C>T variant (Leu 168 Leu) in the subgroup of patients with LPAC syndrome but without an MDR3 gene point mutation suggests that some of them may have been hemizygous for this region, so that a large deletion in exon 6 could be implicated in the disease. Such synonymous single-nucleotide polymorphisms located in coding regions, although seemingly translationally silent, could also have a profound influence on alternative splicing and potentially lead to exon skipping or aberrant splicing. Alternatively, defects in other regions of the gene or in other genes may also be involved, and some evidence from animal studies has pointed to Abcb 11 (previously called the bile salt export pump, BSEP) or Abcc 2 (previously referred to as multidrug resistance related protein 2, or MRP2) as other possible candidate genes underlying susceptibility to cholelithiasis or phospholipid secretion disruption.

Figure 4:
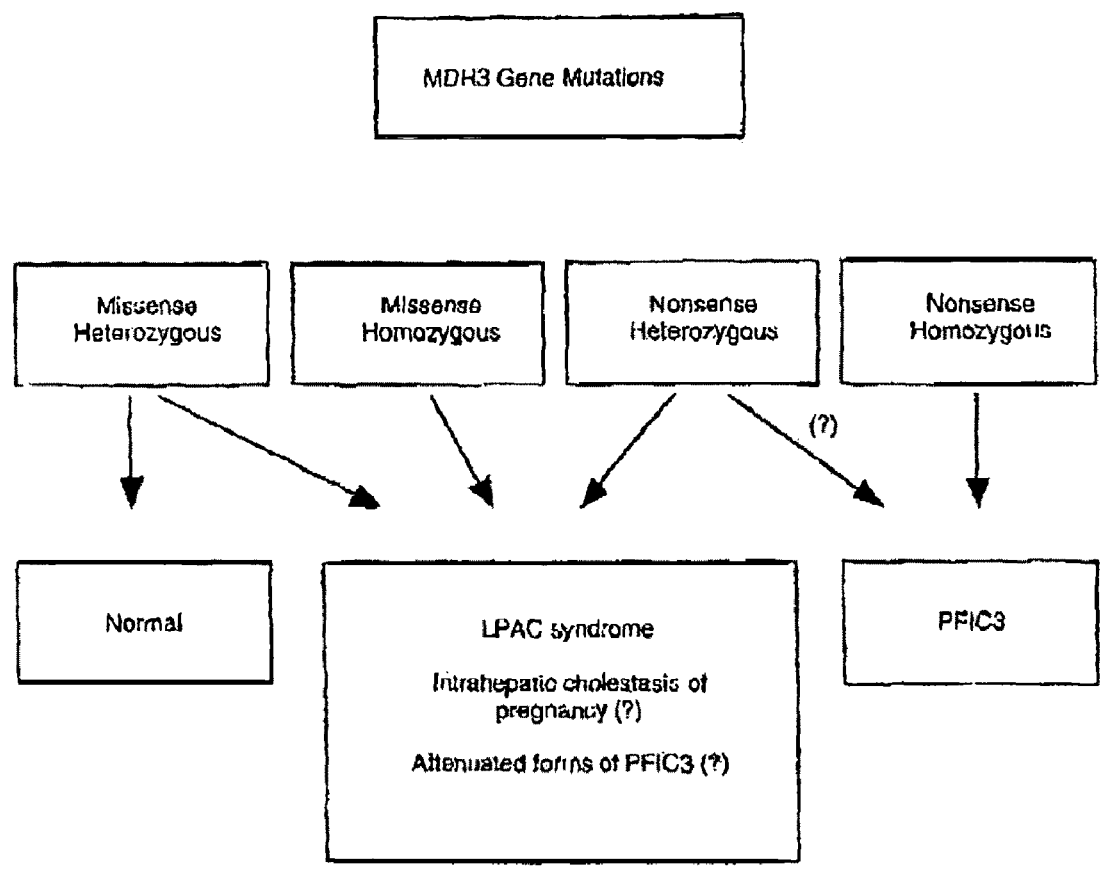
FIG. 4 illustrates MDR3 gene mutations in LPAC and other human liver diseases: genotype-phenotype relationship.

In summary, the results strongly support the role of an MDR3 gene defect in LPAC syndrome and replace it in the context of MDR3 gene-associated liver diseases (see FIG. 4).

All references, patents and patents applications cited herein are expressly incorporated by reference into the present specification in their entireties.

What is claimed is:

1. A method of identifying a human subject with symptomatic cholelithiasis who is susceptible to hepatic syndrome, wherein said hepatic syndrome is characterized by cholesterol microcholelithiasis, intrahepatic cholestasis and one or more mutations of the MDR3 gene, the method comprising:

obtaining a sample of nucleic acids extracted from the human subject; and detecting in the sample of nucleic acids the presence of a missense mutation C959T in exon 9 of the MDR3 gene leading to a S320F amino acid substitution; and identifying the human subject as susceptible to hepatic syndrome if the C959T missense mutation is detected.

2. The method of claim 1 wherein said detecting step comprises:
(a) amplifying the sample of nucleic acids with a pair of primers consisting of SEQ ID NO: 3 and SEQ ID NO: 4 generating a 210 bp fragment of exon 9;
(b) detecting said mutation in exon 9 in the amplified product produced in step a).

3. The method of claim 2, wherein the detection step is carried out upon said sample of nucleic acids using an assay selected from the group consisting of sequencing, digestion with one or more restriction endonucleases, DNA sequencing, and multiplex PCR followed by a ligase detection reaction.

4. The method of claim 1, wherein said human subject is a young adult.

* * * * *

SEQUENCE LISTING

<160> NUMBER OF SEQ ID NOS: 66

<210> SEQ ID NO 1
<211> LENGTH: 21
<212> TYPE: DNA
<213> ORGANISM: Artificial sequence
<220> FEATURE:
<223> OTHER INFORMATION: Amplification Primer

<400> SEQUENCE: 1
ctactcagga ttgggtgctg g                                    21

<210> SEQ ID NO 2
<211> LENGTH: 19
<212> TYPE: DNA
<213> ORGANISM: Artificial sequence
<220> FEATURE:
<223> OTHER INFORMATION: Amplification Primer -continued

```
<400> SEQUENCE: 2
gctagaacat ggctgccag                                                  19

<210> SEQ ID NO 3
<211> LENGTH: 20
<212> TYPE: DNA
<213> ORGANISM: Artificial sequence
<220> FEATURE:
<223> OTHER INFORMATION: Amplification Primer

<400> SEQUENCE: 3
ccctctcatt tttctggtag                                                 20

<210> SEQ ID NO 4
<211> LENGTH: 20
<212> TYPE: DNA
<213> ORGANISM: Artificial sequence
<220> FEATURE:
<223> OTHER INFORMATION: Amplification Primer

<400> SEQUENCE: 4
gttaggagaa ctacttactg                                                 20

<210> SEQ ID NO 5
<211> LENGTH: 20
<212> TYPE: DNA
<213> ORGANISM: Artificial sequence
<220> FEATURE:
<223> OTHER INFORMATION: Amplification Primer

<400> SEQUENCE: 5
ccttacagat cttgaagggc                                                 20

<210> SEQ ID NO 6
<211> LENGTH: 20
<212> TYPE: DNA
<213> ORGANISM: Artificial sequence
<220> FEATURE:
<223> OTHER INFORMATION: Amplification Primer

<400> SEQUENCE: 6
gcttggttct tcccacttac                                                 20

<210> SEQ ID NO 7
<211> LENGTH: 23
<212> TYPE: DNA
<213> ORGANISM: Artificial sequence
<220> FEATURE:
<223> OTHER INFORMATION: Amplification Primer

<400> SEQUENCE: 7
cctgccagac acgcgcgagg ttc                                             23

<210> SEQ ID NO 8
<211> LENGTH: 25
<212> TYPE: DNA
<213> ORGANISM: Artificial sequence
<220> FEATURE:
<223> OTHER INFORMATION: Amplification Primer

<400> SEQUENCE: 8
cttcaagtcc atcggtttcc acatc                                           25
```

```
<210> SEQ ID NO 9
<211> LENGTH: 19
<212> TYPE: DNA
<213> ORGANISM: Artificial sequence
<220> FEATURE:
<223> OTHER INFORMATION: Amplification Primer

<400> SEQUENCE: 9
ccttgtcgct gctaaatcc                                                19

<210> SEQ ID NO 10
<211> LENGTH: 21
<212> TYPE: DNA
<213> ORGANISM: Artificial sequence
<220> FEATURE:
<223> OTHER INFORMATION: Amplification Primer

<400> SEQUENCE: 10
ggctcttctg acacatttgt g                                             21

<210> SEQ ID NO 11
<211> LENGTH: 20
<212> TYPE: DNA
<213> ORGANISM: Artificial sequence
<220> FEATURE:
<223> OTHER INFORMATION: Amplification Primer

<400> SEQUENCE: 11
ggaattggtg acaaggttgg                                               20

<210> SEQ ID NO 12
<211> LENGTH: 25
<212> TYPE: DNA
<213> ORGANISM: Artificial sequence
<220> FEATURE:
<223> OTHER INFORMATION: Amplification Primer

<400> SEQUENCE: 12
gctatttcag caaacatttc catgg                                         25

<210> SEQ ID NO 13
<211> LENGTH: 22
<212> TYPE: DNA
<213> ORGANISM: Artificial sequence
<220> FEATURE:
<223> OTHER INFORMATION: Amplification Primer

<400> SEQUENCE: 13
gctaacgtca agatcttgaa gg                                            22

<210> SEQ ID NO 14
<211> LENGTH: 18
<212> TYPE: DNA
<213> ORGANISM: Artificial sequence
<220> FEATURE:
<223> OTHER INFORMATION: Amplification Primer

<400> SEQUENCE: 14
gaggccaacg cctatgag                                                 18

<210> SEQ ID NO 15
<211> LENGTH: 17
<212> TYPE: DNA
<213> ORGANISM: Artificial sequence
<220> FEATURE:
<223> OTHER INFORMATION: MDR3-SENS2
```

```
<400> SEQUENCE: 15
ggagagggtg tacttgg                                                  17

<210> SEQ ID NO 16
<211> LENGTH: 20
<212> TYPE: DNA
<213> ORGANISM: Artificial sequence
<220> FEATURE:
<223> OTHER INFORMATION: MDR3-AS2

<400> SEQUENCE: 16
aggcatcaac cgatttttac                                               20

<210> SEQ ID NO 17
<211> LENGTH: 20
<212> TYPE: DNA
<213> ORGANISM: Artificial sequence
<220> FEATURE:
<223> OTHER INFORMATION: MDR3-SENS3

<400> SEQUENCE: 17
ctttgtagta ccttcgacag                                               20

<210> SEQ ID NO 18
<211> LENGTH: 20
<212> TYPE: DNA
<213> ORGANISM: Artificial sequence
<220> FEATURE:
<223> OTHER INFORMATION: MDR3-AS3

<400> SEQUENCE: 18
ttgtgctcaa gcaaccctcc                                               20

<210> SEQ ID NO 19
<211> LENGTH: 20
<212> TYPE: DNA
<213> ORGANISM: Artificial sequence
<220> FEATURE:
<223> OTHER INFORMATION: MDR3-SENS4

<400> SEQUENCE: 19
gaggagaaat tccattccac                                               20

<210> SEQ ID NO 20
<211> LENGTH: 20
<212> TYPE: DNA
<213> ORGANISM: Artificial sequence
<220> FEATURE:
<223> OTHER INFORMATION: MDR3-AS4

<400> SEQUENCE: 20
caactcccaa attttaccc                                                20

<210> SEQ ID NO 21
<211> LENGTH: 18
<212> TYPE: DNA
<213> ORGANISM: Artificial sequence
<220> FEATURE:
<223> OTHER INFORMATION: MDR3-SENS5

<400> SEQUENCE: 21
taaaaacctg gcaatgcc                                                 18
```

```
<210> SEQ ID NO 22
<211> LENGTH: 22
<212> TYPE: DNA
<213> ORGANISM: Artificial sequence
<220> FEATURE:
<223> OTHER INFORMATION: MDR3-AS5

<400> SEQUENCE: 22
aactctgtaa ttggaaatta tc                                              22

<210> SEQ ID NO 23
<211> LENGTH: 21
<212> TYPE: DNA
<213> ORGANISM: Artificial sequence
<220> FEATURE:
<223> OTHER INFORMATION: MDR3-SENS6

<400> SEQUENCE: 23
ccatcatgga gctcatcact t                                               21

<210> SEQ ID NO 24
<211> LENGTH: 20
<212> TYPE: DNA
<213> ORGANISM: Artificial sequence
<220> FEATURE:
<223> OTHER INFORMATION: MDR3-AS6

<400> SEQUENCE: 24
gctgccagat gatcgatttc                                                 20

<210> SEQ ID NO 25
<211> LENGTH: 20
<212> TYPE: DNA
<213> ORGANISM: Artificial sequence
<220> FEATURE:
<223> OTHER INFORMATION: MDR3-SENS7

<400> SEQUENCE: 25
gtttgttgga tgtctacttc                                                 20

<210> SEQ ID NO 26
<211> LENGTH: 20
<212> TYPE: DNA
<213> ORGANISM: Artificial sequence
<220> FEATURE:
<223> OTHER INFORMATION: MDR3-AS7

<400> SEQUENCE: 26
cctgaacagg tacaagtacg                                                 20

<210> SEQ ID NO 27
<211> LENGTH: 20
<212> TYPE: DNA
<213> ORGANISM: Artificial sequence
<220> FEATURE:
<223> OTHER INFORMATION: MDR3-SENS8

<400> SEQUENCE: 27
gtgcctttaa acttttctcc                                                 20

<210> SEQ ID NO 28
<211> LENGTH: 20
<212> TYPE: DNA
<213> ORGANISM: Artificial sequence
<220> FEATURE:
<223> OTHER INFORMATION: MDR3-AS8
```

```
<400> SEQUENCE: 28
cgagaagggt taatattagg                                             20

<210> SEQ ID NO 29
<211> LENGTH: 18
<212> TYPE: DNA
<213> ORGANISM: Artificial sequence
<220> FEATURE:
<223> OTHER INFORMATION: MDR3-SENS9

<400> SEQUENCE: 29
gccgagtgtg actcggac                                               18

<210> SEQ ID NO 30
<211> LENGTH: 22
<212> TYPE: DNA
<213> ORGANISM: Artificial sequence
<220> FEATURE:
<223> OTHER INFORMATION: MDR3-AS9

<400> SEQUENCE: 30
ggtctaacca catgctattt tc                                          22

<210> SEQ ID NO 31
<211> LENGTH: 20
<212> TYPE: DNA
<213> ORGANISM: Artificial sequence
<220> FEATURE:
<223> OTHER INFORMATION: MDR3-SENS10

<400> SEQUENCE: 31
ctatgttaca tatacatcac                                             20

<210> SEQ ID NO 32
<211> LENGTH: 23
<212> TYPE: DNA
<213> ORGANISM: Artificial sequence
<220> FEATURE:
<223> OTHER INFORMATION: MDR3-AS10

<400> SEQUENCE: 32
gtacaactta ttcaatgtag ttg                                         23

<210> SEQ ID NO 33
<211> LENGTH: 23
<212> TYPE: DNA
<213> ORGANISM: Artificial sequence
<220> FEATURE:
<223> OTHER INFORMATION: MDR3-SENS11-12

<400> SEQUENCE: 33
gacattccag gtcctatttt tgg                                         23

<210> SEQ ID NO 34
<211> LENGTH: 20
<212> TYPE: DNA
<213> ORGANISM: Artificial sequence
<220> FEATURE:
<223> OTHER INFORMATION: MDR3-AS11-12

<400> SEQUENCE: 34
gcttggttct tcccacttac                                             20
```

<210> SEQ ID NO 35
<211> LENGTH: 18
<212> TYPE: DNA
<213> ORGANISM: Artificial sequence
<220> FEATURE:
<223> OTHER INFORMATION: MDR3-SENS13

<400> SEQUENCE: 35
ggtaggatgt ttttcatg                                                   18

<210> SEQ ID NO 36
<211> LENGTH: 20
<212> TYPE: DNA
<213> ORGANISM: Artificial sequence
<220> FEATURE:
<223> OTHER INFORMATION: MDR3-AS13

<400> SEQUENCE: 36
cctttgaaga ataaactcag                                                 20

<210> SEQ ID NO 37
<211> LENGTH: 19
<212> TYPE: DNA
<213> ORGANISM: Artificial sequence
<220> FEATURE:
<223> OTHER INFORMATION: MDR3-SENS14

<400> SEQUENCE: 37
gacaaagctc catgttgtc                                                  19

<210> SEQ ID NO 38
<211> LENGTH: 20
<212> TYPE: DNA
<213> ORGANISM: Artificial sequence
<220> FEATURE:
<223> OTHER INFORMATION: MDR3-AS14

<400> SEQUENCE: 38
ctgtttctca gcccagactc                                                 20

<210> SEQ ID NO 39
<211> LENGTH: 19
<212> TYPE: DNA
<213> ORGANISM: Artificial sequence
<220> FEATURE:
<223> OTHER INFORMATION: MDR3-SENS15

<400> SEQUENCE: 39
atccaagtgc ttaactgtg                                                  19

<210> SEQ ID NO 40
<211> LENGTH: 19
<212> TYPE: DNA
<213> ORGANISM: Artificial sequence
<220> FEATURE:
<223> OTHER INFORMATION: MDR3-AS15

<400> SEQUENCE: 40
gtatagcatt cactggatc                                                  19

<210> SEQ ID NO 41
<211> LENGTH: 19
<212> TYPE: DNA
<213> ORGANISM: Artificial sequence
<220> FEATURE:
<223> OTHER INFORMATION: MDR3-SENS16

```
<400> SEQUENCE: 41
tacatccatt tggagacac                                               19

<210> SEQ ID NO 42
<211> LENGTH: 17
<212> TYPE: DNA
<213> ORGANISM: Artificial sequence
<220> FEATURE:
<223> OTHER INFORMATION: MDR3-AS16

<400> SEQUENCE: 42
gcaaggctaa gaatttc                                                 17

<210> SEQ ID NO 43
<211> LENGTH: 19
<212> TYPE: DNA
<213> ORGANISM: Artificial sequence
<220> FEATURE:
<223> OTHER INFORMATION: MDR3-SENS17

<400> SEQUENCE: 43
gccttttcta tgtctacag                                               19

<210> SEQ ID NO 44
<211> LENGTH: 17
<212> TYPE: DNA
<213> ORGANISM: Artificial sequence
<220> FEATURE:
<223> OTHER INFORMATION: MDR3-AS17

<400> SEQUENCE: 44
agaagcagca gctgatg                                                 17

<210> SEQ ID NO 45
<211> LENGTH: 20
<212> TYPE: DNA
<213> ORGANISM: Artificial sequence
<220> FEATURE:
<223> OTHER INFORMATION: MDR3-SENS18

<400> SEQUENCE: 45
ctcaagccac tatttatgag                                              20

<210> SEQ ID NO 46
<211> LENGTH: 21
<212> TYPE: DNA
<213> ORGANISM: Artificial sequence
<220> FEATURE:
<223> OTHER INFORMATION: MDR3-AS18

<400> SEQUENCE: 46
agaatttgga agctccatta g                                            21

<210> SEQ ID NO 47
<211> LENGTH: 19
<212> TYPE: DNA
<213> ORGANISM: Artificial sequence
<220> FEATURE:
<223> OTHER INFORMATION: MDR3-SENS19

<400> SEQUENCE: 47
caactcataa ctttgctac                                               19
```

```
<210> SEQ ID NO 48
<211> LENGTH: 24
<212> TYPE: DNA
<213> ORGANISM: Artificial sequence
<220> FEATURE:
<223> OTHER INFORMATION: MDR3-AS19

<400> SEQUENCE: 48
catgcatatc gacataacaa taag                                          24

<210> SEQ ID NO 49
<211> LENGTH: 20
<212> TYPE: DNA
<213> ORGANISM: Artificial sequence
<220> FEATURE:
<223> OTHER INFORMATION: MDR3-SENS20

<400> SEQUENCE: 49
ggtctcccct aaatttcctc                                               20

<210> SEQ ID NO 50
<211> LENGTH: 21
<212> TYPE: DNA
<213> ORGANISM: Artificial sequence
<220> FEATURE:
<223> OTHER INFORMATION: MDR3-AS20

<400> SEQUENCE: 50
caagtgtggg tatgctacat g                                             21

<210> SEQ ID NO 51
<211> LENGTH: 19
<212> TYPE: DNA
<213> ORGANISM: Artificial sequence
<220> FEATURE:
<223> OTHER INFORMATION: MDR3-SENS21

<400> SEQUENCE: 51
gctggagcgc atgcatttg                                                19

<210> SEQ ID NO 52
<211> LENGTH: 17
<212> TYPE: DNA
<213> ORGANISM: Artificial sequence
<220> FEATURE:
<223> OTHER INFORMATION: MDR3-AS21

<400> SEQUENCE: 52
gttgtagtgg gcacaaa                                                  17

<210> SEQ ID NO 53
<211> LENGTH: 22
<212> TYPE: DNA
<213> ORGANISM: Artificial sequence
<220> FEATURE:
<223> OTHER INFORMATION: MDR3-SENS22

<400> SEQUENCE: 53
cttgaacaga ttatgccttt gg                                            22

<210> SEQ ID NO 54
<211> LENGTH: 20
<212> TYPE: DNA
<213> ORGANISM: Artificial sequence
<220> FEATURE:
<223> OTHER INFORMATION: MDR3-AS22
```

```
<400> SEQUENCE: 54
tcctagtcac atcaaaaagc                                               20

<210> SEQ ID NO 55
<211> LENGTH: 17
<212> TYPE: DNA
<213> ORGANISM: Artificial sequence
<220> FEATURE:
<223> OTHER INFORMATION: MDR3-SENS23

<400> SEQUENCE: 55
cttaaaccca ctcggcc                                                  17

<210> SEQ ID NO 56
<211> LENGTH: 23
<212> TYPE: DNA
<213> ORGANISM: Artificial sequence
<220> FEATURE:
<223> OTHER INFORMATION: MDR3-AS23

<400> SEQUENCE: 56
cacaggagtc attttttcc tac                                            23

<210> SEQ ID NO 57
<211> LENGTH: 20
<212> TYPE: DNA
<213> ORGANISM: Artificial sequence
<220> FEATURE:
<223> OTHER INFORMATION: MDR3-SENS24

<400> SEQUENCE: 57
gactttcaaa catcatggag                                               20

<210> SEQ ID NO 58
<211> LENGTH: 20
<212> TYPE: DNA
<213> ORGANISM: Artificial sequence
<220> FEATURE:
<223> OTHER INFORMATION: MDR3-AS24

<400> SEQUENCE: 58
cttatcctgt agctataatc                                               20

<210> SEQ ID NO 59
<211> LENGTH: 19
<212> TYPE: DNA
<213> ORGANISM: Artificial sequence
<220> FEATURE:
<223> OTHER INFORMATION: MDR3-SENS25

<400> SEQUENCE: 59
ctggcaccag aactatacc                                                19

<210> SEQ ID NO 60
<211> LENGTH: 22
<212> TYPE: DNA
<213> ORGANISM: Artificial sequence
<220> FEATURE:
<223> OTHER INFORMATION: MDR3-AS25

<400> SEQUENCE: 60
attatgacaa tattggttgg gc                                            22
```

```
<210> SEQ ID NO 61
<211> LENGTH: 16
<212> TYPE: DNA
<213> ORGANISM: Artificial sequence
<220> FEATURE:
<223> OTHER INFORMATION: MDR3-SENS26

<400> SEQUENCE: 61
gaagctgctg acaccc                                                         16

<210> SEQ ID NO 62
<211> LENGTH: 20
<212> TYPE: DNA
<213> ORGANISM: Artificial sequence
<220> FEATURE:
<223> OTHER INFORMATION: MDR3-AS26

<400> SEQUENCE: 62
gaagtgcctt gtccaagttg                                                     20

<210> SEQ ID NO 63
<211> LENGTH: 23
<212> TYPE: DNA
<213> ORGANISM: Artificial sequence
<220> FEATURE:
<223> OTHER INFORMATION: MDR3-SENS27

<400> SEQUENCE: 63
aatagaactg tcaactgtta agc                                                 23

<210> SEQ ID NO 64
<211> LENGTH: 17
<212> TYPE: DNA
<213> ORGANISM: Artificial sequence
<220> FEATURE:
<223> OTHER INFORMATION: MDR3-AS27

<400> SEQUENCE: 64
ttttccccct gtgcttg                                                        17

<210> SEQ ID NO 65
<211> LENGTH: 21
<212> TYPE: DNA
<213> ORGANISM: Artificial sequence
<220> FEATURE:
<223> OTHER INFORMATION: MDR3-SENS28

<400> SEQUENCE: 65
gattagaaag gtaacatttt c                                                   21

<210> SEQ ID NO 66
<211> LENGTH: 18
<212> TYPE: DNA
<213> ORGANISM: Artificial sequence
<220> FEATURE:
<223> OTHER INFORMATION: MDR3-AS28

<400> SEQUENCE: 66
gggtcttcta aattgatc                                                       18
```